US012611232B2

(12) United States Patent
Park

(10) Patent No.: US 12,611,232 B2
(45) Date of Patent: Apr. 28, 2026

(54) BIO-FLEXIBLE SPINAL FIXATION APPARATUS FOR PREVENTING FATIGUE FRACTURE

(71) Applicant: Kyung-Woo Park, Seoul (KR)

(72) Inventor: Kyung-Woo Park, Seoul (KR)

( * ) Notice: Subject to any disclaimer, the term of this patent is extended or adjusted under 35 U.S.C. 154(b) by 219 days.

(21) Appl. No.: 18/329,250

(22) Filed: Jun. 5, 2023

(65) Prior Publication Data

US 2024/0260999 A1     Aug. 8, 2024

(30) Foreign Application Priority Data

Feb. 2, 2023     (KR) ......................... 10-2023-0014178

(51) Int. Cl.
*A61B 17/70*          (2006.01)
(52) U.S. Cl.
CPC ...... *A61B 17/7028* (2013.01); *A61B 17/7005* (2013.01)
(58) Field of Classification Search
CPC ......................... A61B 17/7028; A61B 17/7005
See application file for complete search history.

(56) References Cited

U.S. PATENT DOCUMENTS

| | | |
|---|---|---|
| 2007/0288008 A1 | 12/2007 | Park |
| 2010/0042154 A1 | 2/2010 | Biedermann et al. |
| 2010/0087865 A1* | 4/2010 | Biedermann ...... A61B 17/7046 |
| | | 606/279 |
| 2010/0228289 A1 | 9/2010 | Park |
| 2017/0319236 A1 | 11/2017 | Spitler et al. |
| 2019/0038319 A1* | 2/2019 | Biedermann ........ A61B 17/701 |

FOREIGN PATENT DOCUMENTS

| | | |
|---|---|---|
| JP | 2004-073855 A | 3/2004 |
| KR | 10-0645377 B1 | 11/2006 |
| KR | 10-0645396 B1 | 11/2006 |
| KR | 10-0645398 B1 | 11/2006 |
| KR | 10-0647529 B1 | 11/2006 |
| KR | 10-1507574 B1 | 4/2015 |
| WO | 2006033503 A1 | 3/2006 |

OTHER PUBLICATIONS

Office Action for Japanese Patent Application No. 2023-088652 issued by the Japanese Patent Office on Jul. 23, 2024.
Office Action for Korean Patent Application No. 10-2023-0014178 issued by the Korean Intellectual Property Office (KIPO) on Feb. 12, 2025.

* cited by examiner

*Primary Examiner* — Tessa M Matthews
(74) *Attorney, Agent, or Firm* — IP & T GROUP LLP

(57) ABSTRACT

The present invention relates to a bio-flexible spinal fixation apparatus capable of realizing motions similar to general body mechanical motions during flexion and extension motions after spinal fixation surgery by configuring a center of a coil part of a rod to have a eccentricity at a certain distance from a center line of a straight part and a specific inclination, and conveniently performing an operation of setting a fixing position of the rod during spinal fixation surgery by machining the straight part section of the rod into a flat surface. The present invention includes a screw pike that includes a head part and a screw; a rod that has a straight part and a coil part wound to be inclined by a predetermined angle with an eccentricity from a center of the straight part; and a set screw.

11 Claims, 11 Drawing Sheets

BIO-FLEXIBLE SPINAL FIXATION APPARATUS FOR PREVENTING FATIGUE FRACTURE

CROSS-REFERENCE TO RELATED APPLICATION

This application claims priority under 35 U.S.C. § 119 to Korean Patent Application No. 10-2023-0014178 filed on Feb. 2, 2023, which is incorporated herein by reference in its entirety.

TECHNICAL FIELD

The present invention relates to a bio-flexible spinal fixation apparatus for fixing a damaged or deformed pedicle with a screw pike and a rod, and more particularly, to a bio-flexible spinal fixation apparatus capable of implementing body natural mechanical motions such as flexion and extension by configuring in order for a straight part and a coil part constituting a rod to have a central eccentricity and a specific inclination, refining and simplifying spinal fixation surgery by keeping the coil part of the rod within a certain range of set angle during the spinal fixation surgery, and preventing from occurring the stress caused by a repeated load applied to a contact area between a set screw and the rod due to frequent spinal motions of the surgical patient, subsequently leading to fatigue fracture.

BACKGROUND ART

In general, the spine consists of 24 bones (excluding sacrum and coccyx which are fused segments), which are connected by joint segments, in which discs are located between each joint. By this configuration, the spine not only maintains a posture of a human being while performing a cushioning action and supports a body weight and various loads, but also serves as a basis for motion, and has the important function of protecting internal organs. However, when the spine is damaged or deformed due to artificial factors such as external shock, a degenerative change, or an abnormal posture lasting for a long time, severe pain is caused by compressing nerves passing through a spinal canal or an intervertebral foramen. When these degenerative diseases have progressed beyond a certain level, surgery should be performed so that the damaged or deformed parts of the spinal segments do not press or compress the nerves.

Representative spinal degenerative diseases include spinal stenosis, spondylolisthesis, spondylolysis, etc., accompanied by intersegmental instability, and these degenerative diseases have been treated through spinal fusion using the bio-flexible spinal fixation apparatus.

The spinal fusion using the bio-flexible spinal fixation apparatus will be briefly described with reference to FIGS. 1 and 2.

FIG. 1 is a perspective view illustrating a configuration of a bio-flexible spinal fixation apparatus according to the related art, and FIG. 2 is a schematic diagram illustrating the bio-flexible spinal fixation apparatus according to the related art mounted on a spinal segment.

As illustrated in FIG. 1, the bio-flexible spinal fixation apparatus according to the related art includes a U-shaped receiving groove 101a, a head part 101 having a female thread formed on an inner circumferential surface of the receiving groove 101a, a screw pike 100 having a screw 102 inserted into a pedicle and inserted into the damaged spinal segment, a rod 200 connecting each of the screw pikes 100 to fix a pedicle, a set screw 300 fastened to a female thread formed in the receiving groove 101a to fix the rod 200 and having a wrench insertion groove 300a formed thereon.

As illustrated in FIG. 2, in the bio-flexible spinal fixation apparatus according to the related art, the screw 102 of the screw pike 100 is inserted into and fixed to each pedicle 500, and the rod 200 is seated in the U-shaped receiving groove 101a formed in the head part 101, and then, is fixed with the set screw 300.

In the spinal fusion performed through this series of procedures, the rod 200 plays the most pivotal role in fixing the spine. Therefore, the material or elasticity of the rod has a great influence on the human body after the fusion of the spinal segment.

The conventional rod 200 is configured in a single form to simultaneously connect several pedicle screw pikes, and most of them are made of medical titanium, so the rod itself has no elasticity. For this reason, it is difficult to maintain a natural sagittal balance once the spinal segments are fused according to the shape of the rod after the spinal fixation surgery. In addition, after the complete fusion according to the shape of the rod, since the load is concentrated on the upper or lower segments of the spine where the pedicle screw pike is inserted, there is a problem of causing degenerative changes in adjacent segments such as another spinal stenosis or instability after several years of the fusion. In addition, when an impact is applied to a waist by an external factor, there is a problem that the rod is bent or a neck of the pedicle screw pike is fractured.

Since the rod is manufactured based on the general shape of the spine regardless of the shape of the individual patient's spine, the rod has the difficulty of standardizing each single product and being manufactured in various shapes and lengths, which acts as a factor increasing the manufacturing cost. The rod having the structure causes many difficulties even when connecting to the pedicle screw pike. That is, since each person has a different pedicle shape and conditions of diseases, it is very difficult to mount a rod when the pedicle screw pikes inserted into each segment of the spine are not uniformly aligned. This is related to physical properties of the rod without elasticity. In this case, after adjusting a distance and direction by twisting the screw pike obliquely, or arbitrarily adjusting an angle of the head part by using a polyaxial type screw in which the head part freely rotates around a threaded part within a set angle range, the rod is fixed according to the installation position of the rod. In this way, since the spinal fusion using a straight-type rod requires the precision of surgery in drilling a hole for the screw pike insertion into the pedicle by accurately determining whether the installation position of the screw pike is uniformly located, a burden on a surgeon is increasing. In addition, since it is necessary to spend a lot of time on bending single rods individually according to the curved shape of the pedicle and connecting the rods uniformly according to the installation position of the screw pike, it is a problem that the surgery time becomes long.

In order to overcome the above problems of the rod, the present applicant proposed rods of various shapes through KR Patent No. 10-0645377, KR Patent No. 10-0645396, and KR Patent No. 10-0645398.

As illustrated in FIG. 3, the bio-flexible spinal fixation apparatus presented in the prior patents registered by the present applicant has a structure in which the rod 200 is configured in a segmented form, an elastic part 202 is formed at the center of the rod 200, and two grooves 103a and 103b are formed in the receiving groove 101a of the screw pike 100. In such a conventional bio-flexible spinal fixation apparatus, the segmental rod 200 is continuously connected to the receiving grooves 103a and 103b of the screw pike 100 in a zigzag manner, which granted the mobility between the spinal segments within a certain range by imparting bending deformation of the rod.

The presented prior patents realize the effect of maintaining smooth motion between spinal segments through a cushioning action on spinal motion after the spinal fusion and at the same time increasing the fixation force between the spinal segments.

It was found as a result of many years of clinical trials for the above configurations that, in the course of surgery, the elastic part of the central portion of the rod should be kept symmetrical based on a center line of a human body at an angle inclined by a certain angle with respect to the center line of the rod to double the elastic force of the rod, thereby implementing optimized biomechanics during the surgical patient's spinal motion and effectively limiting a bending angle when bending the waist backward. Therefore, it is very important to fasten the rods with the angles of these rods maintained during the surgery. However, since the cross section of the straight part of the rod, that is, the part in contact with the set screw, is circular, the rod rotates in the process of seating the rod on the screw pike and then tightening the rod with the set screw, which accordingly involves a problem that it is very difficult to precisely set the angle of the elastic part of the central portion of the rod.

In addition, in the process of tightening the rod with the set screw, scratches may occur in the contact area between the set screw and the rod, and the scratches may grow into fine notches due to the elastic motion of the rod for a long-term period to fracture the rod. In particular, the fractured rod cases are frequently caused by the occurrence of intensive notches in the contact area between the set screw and the rod seated in the groove of the screw pike. Explaining these causes in more detail, in the mechanical action of the set screw pressing the rod seated in the groove of the screw pike, it was found that the stress by the repeated load is concentrated on the scratch area generated in the contact area between the set screw and the rod, which leads to fatigue fracture.

The phenomenon in which the stress is concentrated in the contact area between the set screw and the rod is a result confirmed by the present applicant through many years of clinical practice, and the phenomenon that the rod is fractured due to the occurrence of the notch is related to the fact that the contact area between the set screw and the rod having a circular cross section are formed of a point contact. That is, when performing body mechanical motions through flexion, which is a motion of bending a waist forward, and extension, which is a motion of extending the waist, the straight part of the rod moves by a certain angle while the coil part of the rod is elastically operated, causing fatigue at the point contact area for a long-term period, and sequentially the fatigue phenomenon leads to fatigue failure which is a cause of fracturing a road.

Also, the reason why the strength of the contact area between the set screw and the rod becomes weak is due to the strong fixation force of the set screw during the spinal fusion. In other words, it is a problem that the clamping force pressed by the set screw to prevent the rod from moving is not shared uniformly over the entire straight part of the rod and the strength of the point contact area become weak by the load highly concentrated on the contact area between the end face of the set screw and the rod.

RELATED ART DOCUMENT

Patent Document

Korean Patent Publication No. 10-0645377 (registered on Nov. 6, 2006)
Korean Patent Publication No. 10-0645396 (registered on Nov. 6, 2006)
Korean Patent Publication No. 10-0645398 (registered on Nov. 6, 2006)

DISCLOSURE

Technical Problem

Therefore, the present invention provides a bio-flexible spinal fixation apparatus capable of realizing a natural body mechanical motion during flexion and extension after spinal fixation surgery by configuring a straight part of a rod in a position with an eccentricity at a constant interval laterally from a center of a coil part of the rod.

In addition, the present invention provides a bio-flexible spinal fixation apparatus capable of conveniently setting a fixing position of a rod during spinal fixation surgery by processing a portion of a straight part section of the rod contacting a set screw into a flat surface.

In addition, the present invention provides a bio-flexible spinal fixation apparatus that may be naturally maintained symmetrical based on a center line of a human body by positioning coil parts of rods on both sides within a set angle (31.7°±5°) without deviating from a regular alignment line of a head part of a pedicle screw pike.

In addition, the present invention provides a bio-flexible spinal fixation apparatus capable of preventing fatigue fracture caused by a repeated load in a contact area between a set screw and a rod by configuring a washer integrally with the set screw in order to make the contact area between the set screw and the rod form surface contact rather than point contact.

In addition, the present invention provides a bio-flexible spinal fixation apparatus capable of increasing the fixation force between the spinal segments by connecting spinal segments with a rod equipped with a coil part, and at the same time smoothly maintaining motion between the spinal segments.

Technical Solution

In an aspect, the present invention provides a bio-flexible spinal fixation apparatus including: a screw pike that includes a head part that has a receiving part penetrating in both sides and female threads formed on an inner circumferential surface of the receiving part and grooves formed in parallel at a bottom portion and a screw that extends to a bottom surface of the head part and is inserted into a spinal segment to be fixed; a rod that has a straight part seated in the groove of the screw pike and a coil part wound to be inclined by a specific angle based on a center separated by a predetermined distance with an eccentricity from a center of the straight part; and a set screw that has a fixing groove formed in the central portion and is fastened to the female thread of the head part of the screw pike to pressurize and fix the rod.

An upper surface of the straight part of the rod may have a flat surface. When the rod is seated in the groove of the screw pike, the rod may make the flat surface face upward and serve as a reference plane for the mounting position when coupled with the set screw.

The flat surface of the rod may be formed by a compression processing process in which a cross section is decreased by being pressed at a right angle by a compression press or the like.

A diameter of a cross section of the straight part of the rod may be formed larger than that of a cross section of the coil part. Preferably, the diameter of the cross section of the straight part of the rod may be Φ4.5 mm, and the diameter of the cross section of the coil part may be Φ4.0 mm.

The screw pike may be symmetrically inserted into both sides of the spine based on a center line of a human body, and a direction in which the coil part is wound may be opposite to each other based on a center line of the straight part so that the coil part of the rod is symmetrically located on both sides of the spine.

The set screw may be composed of a cylindrical portion having a coupling hole penetrating through the central portion, and the bio-flexible spinal fixation apparatus may further include a washer that has a spherical projection provided on the upper side of the central portion to fit into a coupling hole of the cylindrical portion and is formed in a plane on the bottom surface to be in close contact with the flat surface of the rod in order to uniformly share a vertical load applied by a tightening force of the set screw to the flat surface of the rod.

As another embodiment of the washer according to the present invention, the washer may have a spherical projection on the upper side of the central portion so as to fit into the coupling hole of the set screw and have a spherical groove having a size receiving the spherical surface of the rod formed on the bottom surface in order to surface-contact a vertical load applied by a tightening force of the set screw.

Advantageous Effects

As described above, according to the present invention, there are the following effects.

First, to make a flat surface of the rod seated in a groove of a screw pike face upward during spinal fixation surgery by flattening an upper surface of a straight part of a rod enables the rod easily to be in place and be installed. Accordingly, this prevents the rod from rotating during a coupling process by a tightening force of a set screw and makes it unnecessary to adjust an angle by re-erecting a coil part lying down out of a regular alignment line of a head part of a pedicle screw pike.

More specifically, according to the present invention, it is very important to constantly set the coil part based on a center line of the rod when performing a rod coupling operation of spinal fixation surgery, and to perform a setting operation for fixing position in order that the coil parts of the rods on both sides are kept symmetrical without being biased to one side based on a center line of a human body. This is because the coil part of the rod may limit the bending of the waist when performing an extension motion that bends a body backward after fixing a spine, so a load is not concentrated between several fused spinal segments, and the burden on the waist is relieved.

In this way, to make the flat surface of the rod seated in the groove of the screw pike face upward and tighten the rod with the set screw enables the fixing position of the rod to easily set.

Second, even after the spinal fixation surgery, it implements the load sharing similar to a normal load sharing mechanism of the spine.

An anterior portion of the spine is mainly composed of vertebrae, and a posterior portion of the spine is composed of a spinal canal, facet joint, and processes (transverse process and spinous process), and it is common for a vertical load applied to the spine to be shared in an approximately 8:2 ratio between the anterior and posterior portions. However, when the rigidity of the structure of the posterior portion inserted for the purpose of spinal fusion is high, a stress shielding effect occurs in which most of the load is shared to the posterior portion of the spine, resulting in blocking a natural flow of load sharing or a phenomenon in which the load sharing burdened on the anterior portion and the posterior portion is reversed from 2:8 to 3:7. Since this phenomenon reduces the load applied to the vertebrae of the anterior portion of the spine and weakens micro-motion or stimulus between an interbody fusion cage inserted between the vertebraes for the purpose of spinal fusion and the vertebrae, it is difficult to expect sufficient bony fusion and results such as cage migration or bony fusion failure occur.

According to the present invention, by connecting spinal segments with the rod configured so that the straight part and the coil part have a central eccentricity and a specific inclination, it is possible to implement the load sharing similar to the normal load sharing mechanism. As a result of finite element analysis, it was confirmed that the load sharing ratio between the anterior portion and the posterior portion approached the normal load sharing ratio at a ratio of 7:3 or 7.5:2.5.

Third, since a continuous connection operation of rods configured in the form of segmental connection is possible, it is possible to quickly perform the spinal fixation operation and solve the inconvenience of surgery in the rod coupling process of the conventional surgical method using a rigid rod. Especially, when revision surgery to extend the surgical segment is unavoidable, whereas the previously fastened rod needs to be removed and replaced with a new rod in the case of surgery using a rigid rod, the present invention has the advantage that only the rod of the extended portion needs to be fastened by incising only an area requiring revision surgery thanks to this segmental connection method.

Fourth, by integrally configuring the washer with the set screw so that the load applied to the contact portion of the rod is uniformly shared when the set screw is tightened, it is possible to prevent the contact area between the set screw and the rod from leading to the fatigue fracture by repeated stress.

BEST MODE

Hereinafter, preferred embodiments of the present invention will be described in detail with reference to the accompanying FIGS. 4 to 15.

A bio-flexible spinal fixation apparatus according to the present invention is implemented to simplify an operation of setting fixing position of a rod in a surgical operation of fixing the rod with a set screw, and to prevent the rod from leading to fatigue fracture by repeated stress.

A configuration of a bio-flexible spinal fixation apparatus according to a first embodiment of the present invention will be described with reference to FIGS. 4 to 10.

Figure 1:
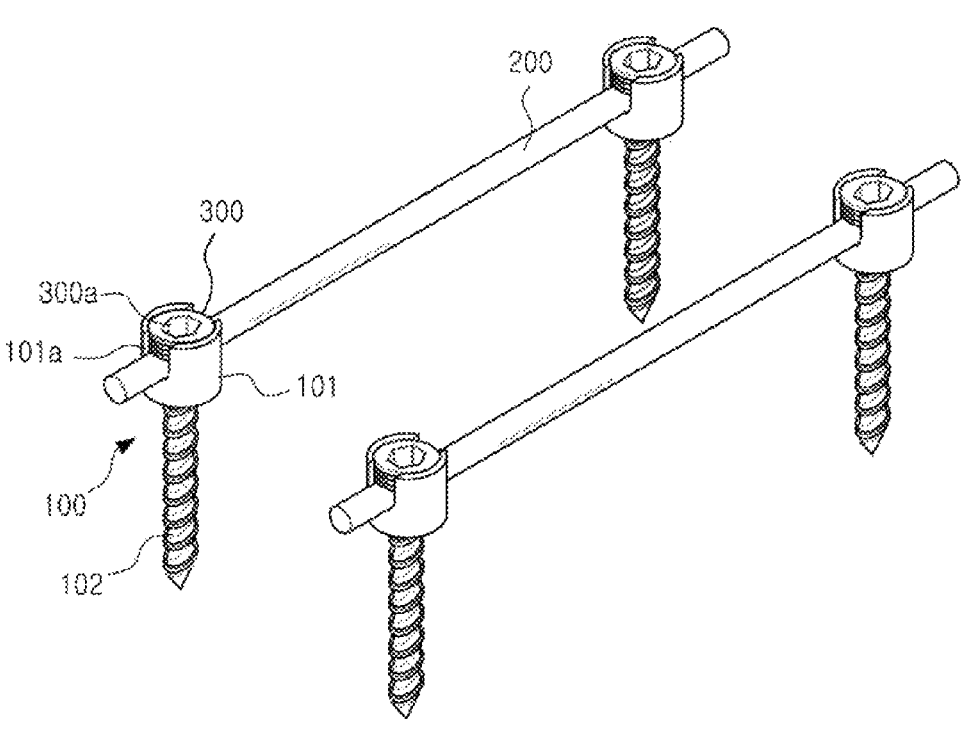
FIG. 1 is a perspective view illustrating a configuration of a bio-flexible spinal fixation apparatus according to the related art.
Figure 2:
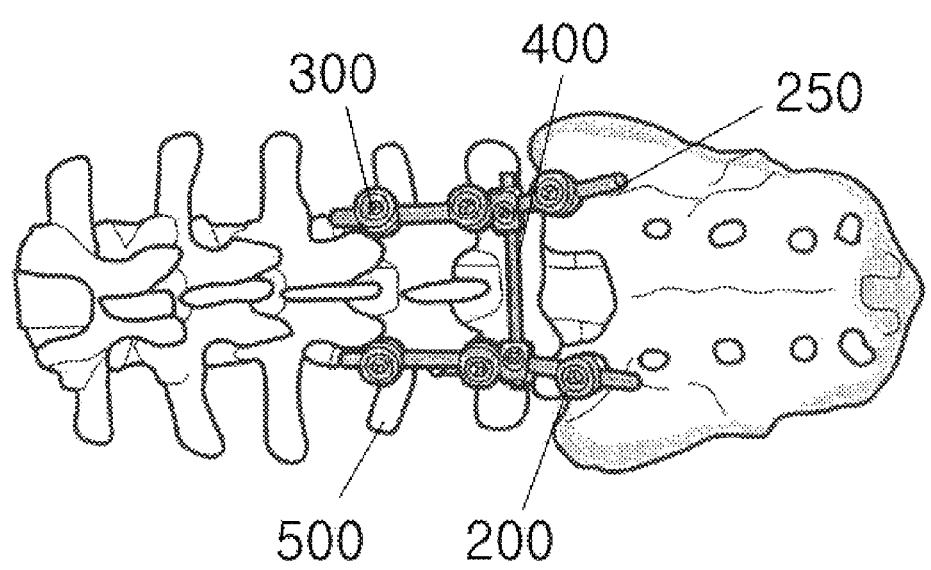
FIG. 2 is a schematic diagram of the bio-flexible spinal fixation apparatus according to the related art mounted on a spinal segment.
Figure 3:
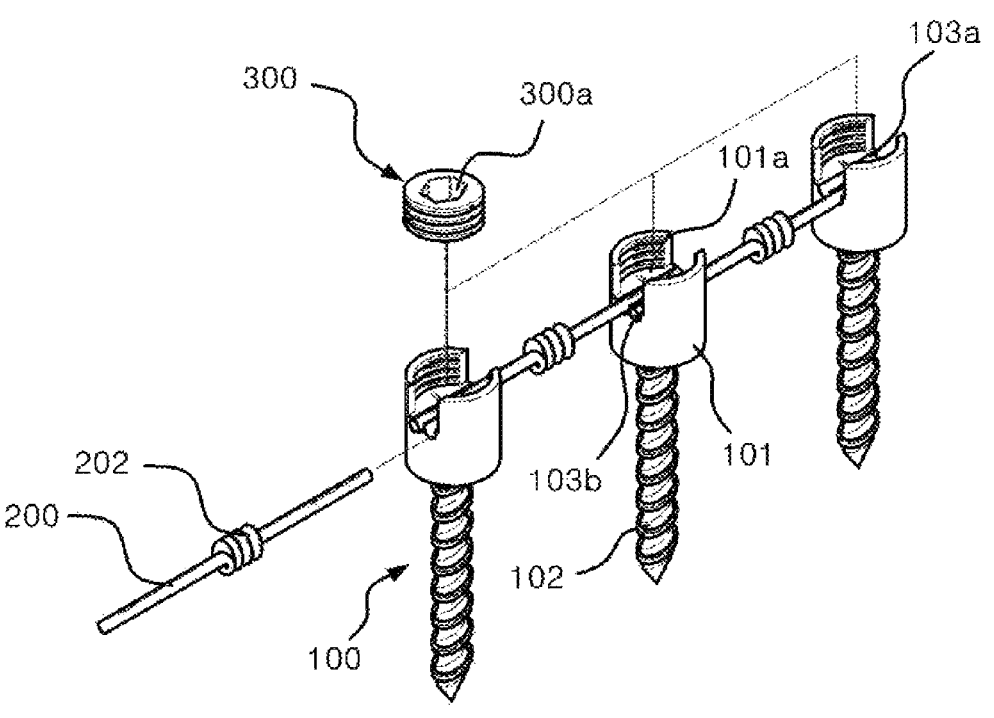
FIG. 3 is an exemplary view illustrating various types of pedicle screw pike rods according to the related art.
Figure 4:
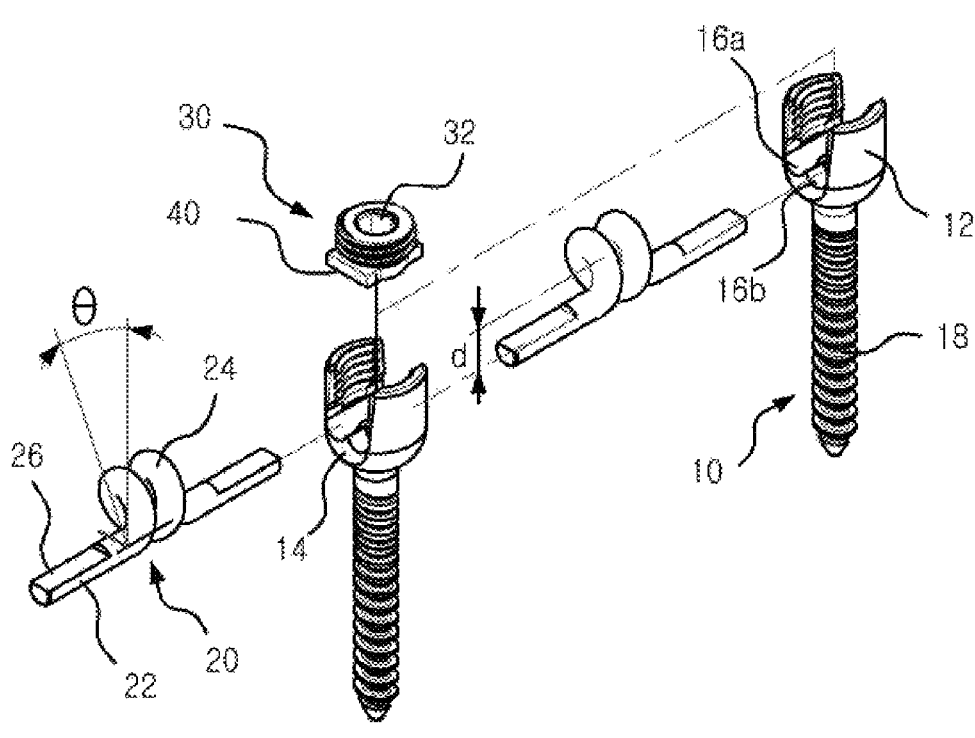
FIG. 4 is a perspective view illustrating a configuration of a bio-flexible spinal fixation apparatus according to an embodiment of the present invention.
Figure 5:
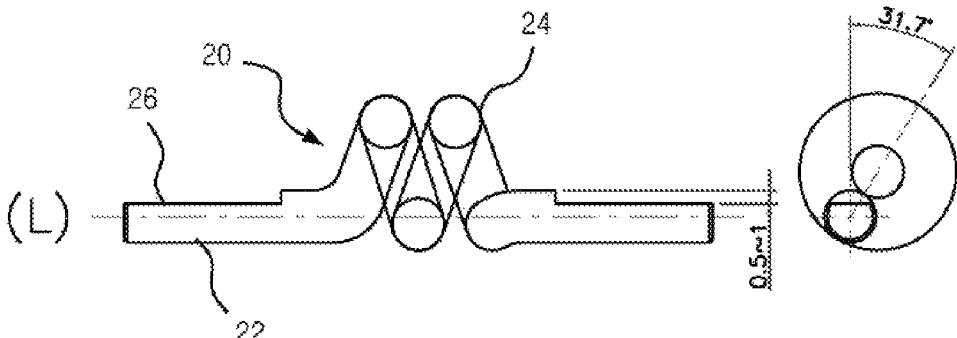
FIG. 5 is a front and right-side projection view illustrating a configuration of a left (L) rod, which is a main part of the bio-flexible spinal fixation apparatus according to the present invention.
Figure 6:
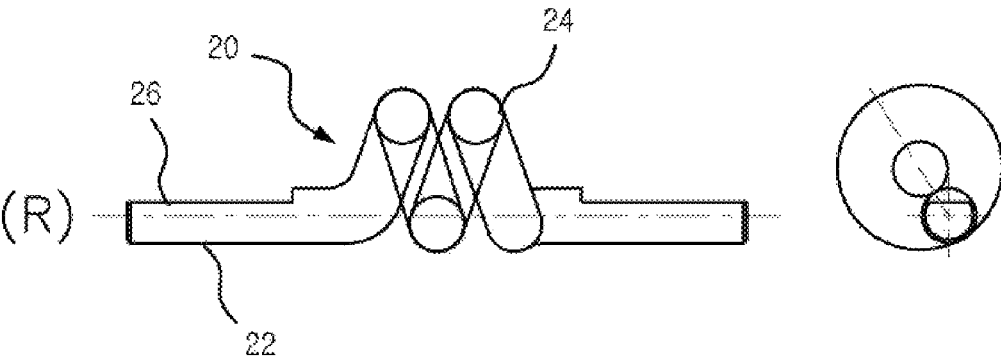
FIG. 6 is a front and right-side projection view illustrating a configuration of a right (R) rod, which is a main part of the bio-flexible spinal fixation apparatus according to the present invention.
Figure 7:
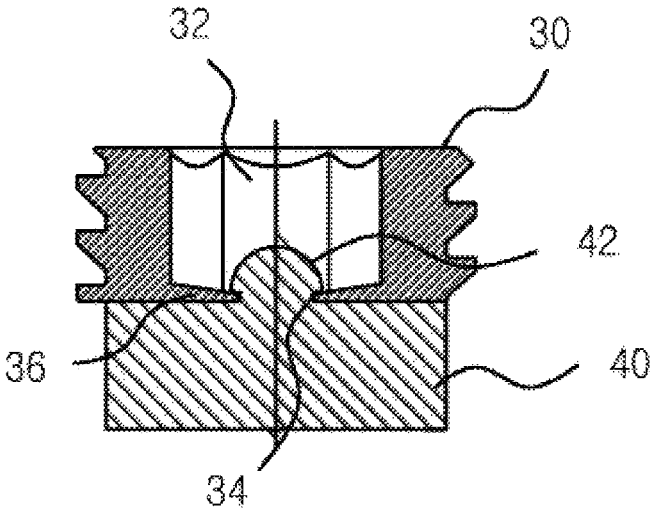
FIG. 7 is a cross-sectional view illustrating a configuration in which a washer is mounted on a set screw, which is a main part of the present invention.
Figure 8:
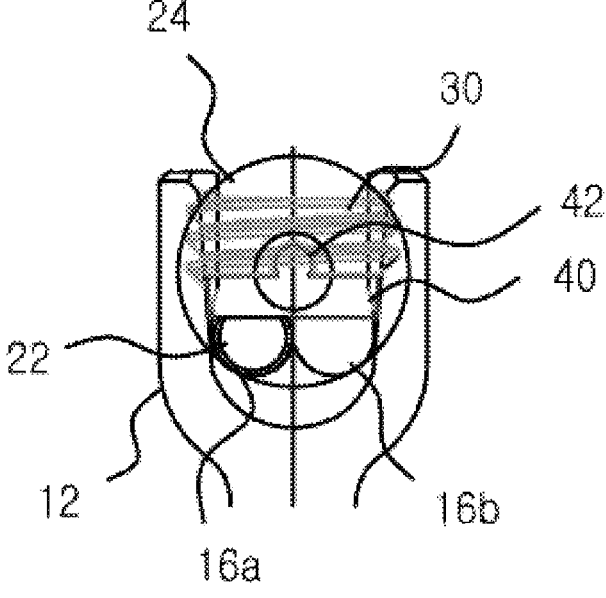
FIG. 8 is a schematic cross-sectional projection view in which a rod and a set screw are coupled to a head part of a screw pike.

FIG. 4 is a perspective view illustrating a configuration of a bio-flexible spinal fixation apparatus according to an embodiment of the present invention, FIG. 5 is a front and right-side projection view illustrating a configuration of a left (L) rod, which is a main part of the bio-flexible spinal fixation apparatus according to the present invention, FIG. 6 is a front and right-side projection view illustrating a configuration of a right (R) rod, which is a main part of the bio-flexible spinal fixation apparatus according to the present invention, FIG. 7 is a cross-sectional view illustrating a configuration in which a washer is mounted on a set screw, which is a main part of the present invention, and FIG. 8 is a schematic cross-sectional projection view in which a rod and a set screw are coupled to a head part of a screw pike.

As illustrated in FIGS. 4 to 6, the bio-flexible spinal fixation apparatus in this embodiment includes: a plurality of screw pikes 10 that include a head part 12 that has a U-shaped receiving groove 14 penetrating in a longitudinal direction and having a female screw formed on an inner circumferential surface thereof and two grooves 16a and 16b formed at the bottom of the receiving groove 14 and screws 18 that are symmetrically inserted into a spinal segment based on a center line of a human body; a straight part 22 that is seated in the grooves 16a and 16b of the screw pike 10; a rod 20 that has a coil part 24 wound to the left (L) or right (R) based on a center with a certain eccentricity d from a center of the straight part 22 and is coupled to the screw pike 10; a set screw 30 that is fastened to the receiving groove 14 of the head part 12 and has a wrench groove 32 formed in a central portion; and a washer 40 that is integrally coupled to a bottom surface of the set screw 30 and applies a fixed load to the straight part 22 of the rod 20 with uniform sharing when the set screw 30 is fastened.

In the bio-flexible spinal fixation apparatus of the present invention described above, the screw pikes 10 are symmetrically inserted into both sides of a spine 500 segment in a transverse direction based on a center line of a human body, and the rod 20 is seated in the grooves 16a and 16b of the receiving groove 14 in a zigzag manner to connect each spinal segment in the longitudinal direction.

In the embodiment of the present invention, the coil part 24 of the rod 20 is wound twice, and the straight parts 22 on both sides have a flat surface 26 whose upper portion is flat to set the standard for the fixing position of the rod 20. When the rod 20 is fixed with the flat surface 26 facing upward, the coil part 24 is automatically erected at an inclination of about 31.7°±5° from the center line of the straight part 22, and the coil parts 24 of the rods 20 on both sides of the left and right are symmetrically fixed on both sides based on the center line of the human body.

As illustrated in FIG. 7, the set screw 30 has a through hole 34 having a wing part 36 formed at the center of the bottom surface. The washer 40 has an angular shape with a size to be inserted into the receiving groove 14, and a spherical projection 42 is formed on the upper portion to fit into the through hole 34 of the set screw 30. In this case, the wing part 36 of the through hole 34 and the spherical projection 42 are configured to have a gap, so that the set screw 30 rotates and is fastened to a female screw of the head part 12, but the washer 40 descends without rotating and presses the flat surface 26 of the rod 20 with a uniform load. Accordingly, it is possible to prevent scratch areas generated on a contact surface of the rod 20 due to rotational force resulting from fastening of the set screw 30 from leading to a notch due to repetitive elastic operation of the rod 20.

In more detail, as illustrated in FIG. 8, even though the tightening force is provided through the set screw 30, since a rotating surface of the set screw 30 contacts only the washer 40, scratches caused by the rotating surface of the set screw 30 are not transmitted to the rod 20. In addition, since the uniformly shared load pressed by the washer 40 is applied to the entire contact surface area of the flat surface 26 of the rod 20, it is possible to prevent the repeated stress occurred when a human waist is bent and stretched as in the related art from concentrated on the point contact area and sequentially leading to the fatigue fracture.

Figure 9:
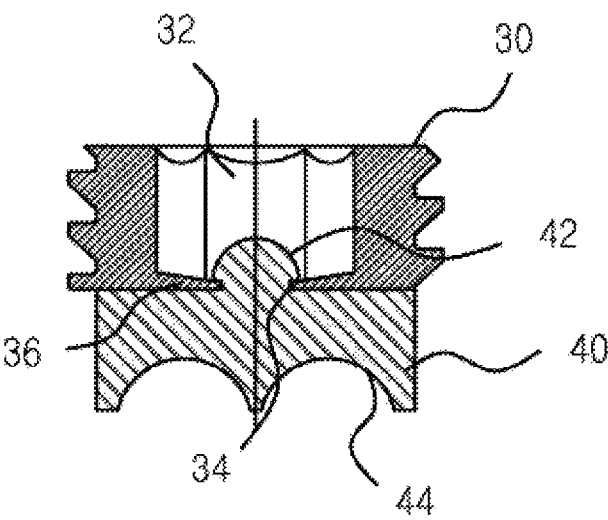
FIG. 9 is a diagram illustrating another example of a configuration in which the set screw and washer of FIG. 7 are integrated.

Meanwhile, a configuration of another embodiment of the washer 40 integrally coupled to the set screw 30 is illustrated in FIG. 9.

In this embodiment, a structure is proposed in which a spherical groove 44 of a size capable of surrounding an outer diameter of the rod is formed on the bottom surface of the washer 40.

According to the spherical groove 44 of the washer 40, in case that a flat surface 26 is not formed on the straight part 22 of the rod 20 and seated in the grooves 16a and 16b of the head part 12, the spherical groove 44 is in surface contact t with the straight part 22 of the spherical cross section without the flat surface 26 to uniformly share the load of the set screw 30 to the straight part 22.

Figure 10:
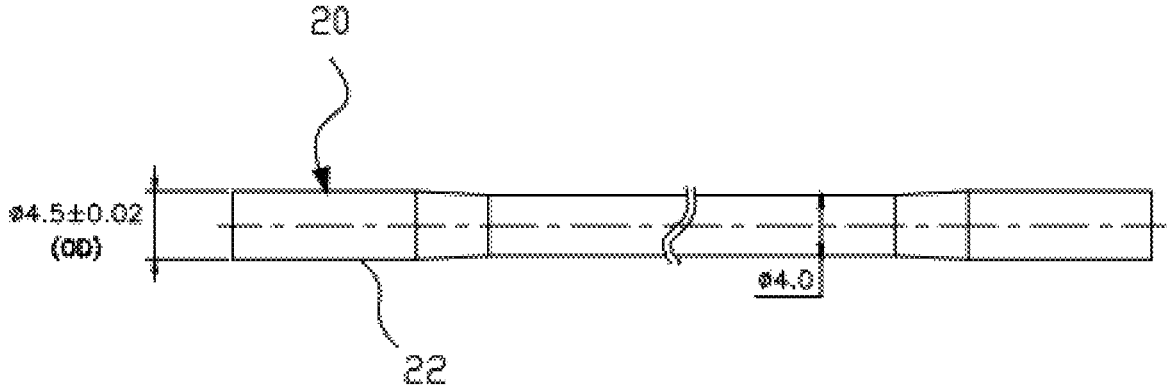
FIG. 10 is a view of a straight state before molding a coil part on the rod of the present invention.
Figure 11:
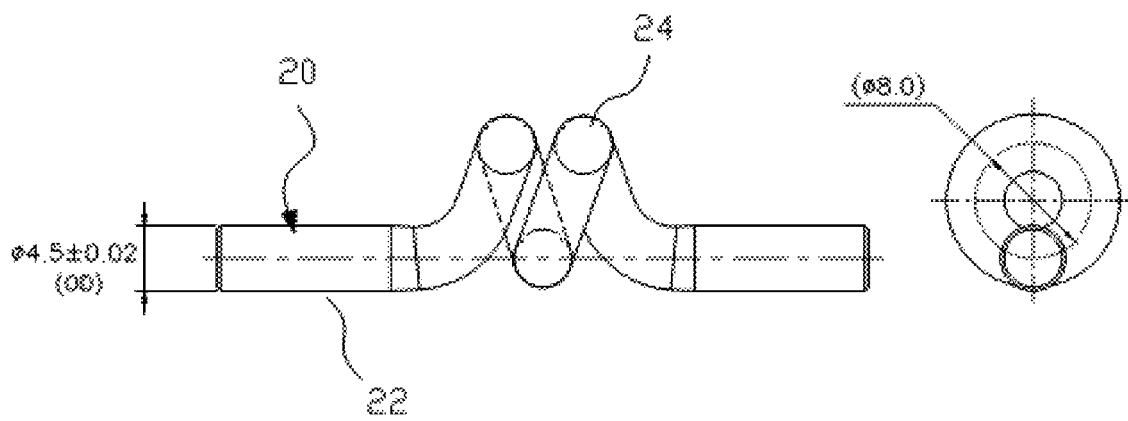
FIG. 11 is a view after molding in which the coil part is wound twice around the rod of the present invention.
Figure 12:
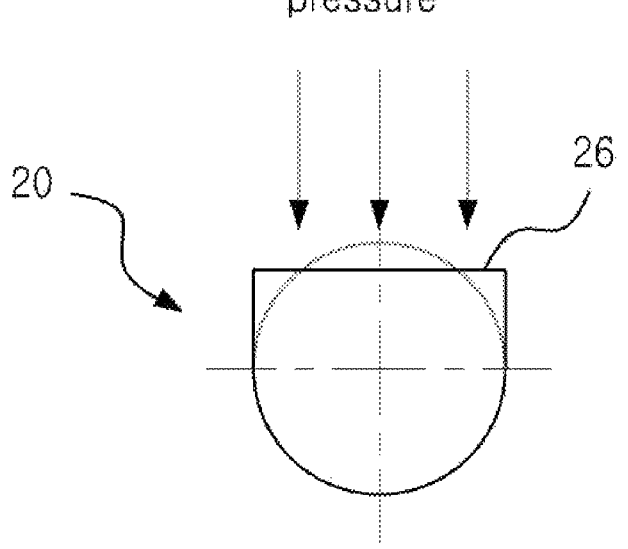
FIG. 12 is a diagram illustrating an example of machining a flat surface on a straight part of a rod, which is the main part of the present invention.
Figure 13:
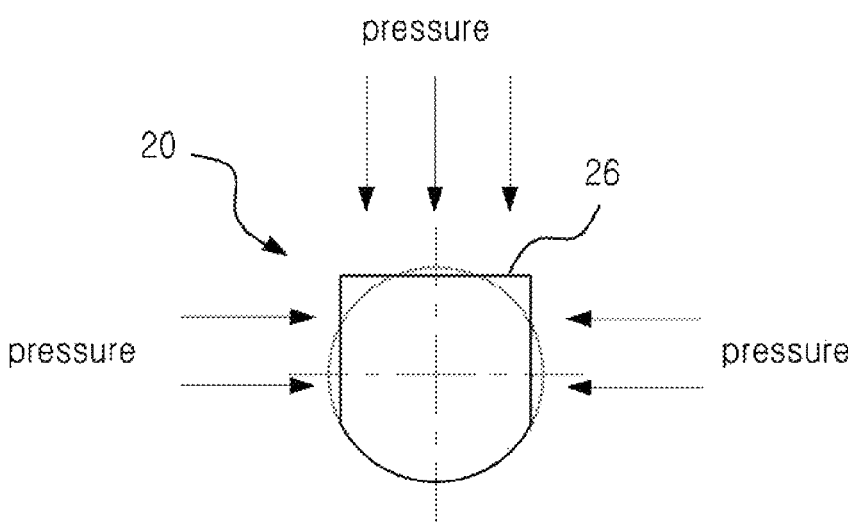
FIG. 13 is a diagram illustrating another example of machining the flat surface.

FIG. 10 is a view of a straight state before molding the coil part 24 on the rod of the present invention, FIG. 11 is a view after molding in which the coil part 24 is wound twice around the rod of the present invention, FIG. 12 is a diagram illustrating an example of machining a flat surface on a straight part of a rod, which is the main part of the present invention, and FIG. 13 is a diagram illustrating another example of machining the flat surface.

As illustrated in FIGS. 10 and 11, in the embodiment of the present invention, a structure in which a diameter of a cross section of the straight part 22 section of the rod 20 is larger than that of a cross section of the coil part 24 section is proposed. Clinically observed at a point where a long-term period has elapsed after spinal fixation surgery, this is to ensure that the fixing operation of the rod 20 maintains maximum rigidity within an allowable range in order to delay the time when the fatigue fracture of the straight part 22 occurs or semi-permanently maintain. In this embodiment, a structure in which the diameter of the cross section of the straight part 22 is Φ4.5 mm and the diameter of the cross section of the coil part 24 is Φ4.0 mm is proposed.

In addition, as illustrated in FIG. 12, the straight part 22 of the rod 20 whose diameter has been increased to maintain rigidity is machined to flatten the upper surface by pressing with a machine such as a compression press so that there is no loss of diameter. As illustrated in FIG. 13, as another example of the flat surface 26, except for the lower round surface, both the upper and side surfaces may be pressed with a compression press or the like to be machined in an angular shape.

Figure 15:
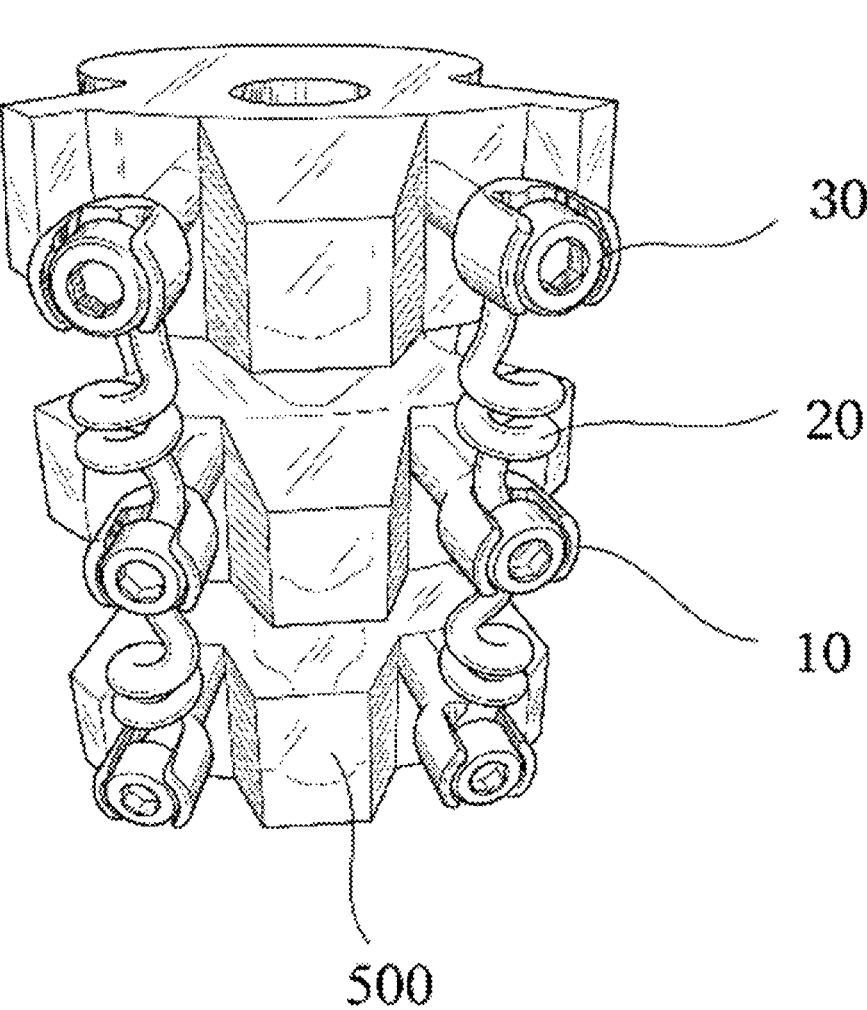
FIG. 15 is a model diagram illustrating a state in which the bio-flexible spinal fixation apparatus according to the present invention is mounted on the spine.

As described above, according to the configuration of the rod 20, as illustrated in FIG. 15, since the operation of setting the fixing position in which the coil parts 24 of the rods 20 on both sides are not biased to one side and are maintained symmetrically based on the center line of the human body may be easily performed based on the flat surface 26 of the rod, it is possible to simplify the coupling operation of the rod 20.

Figure 14:
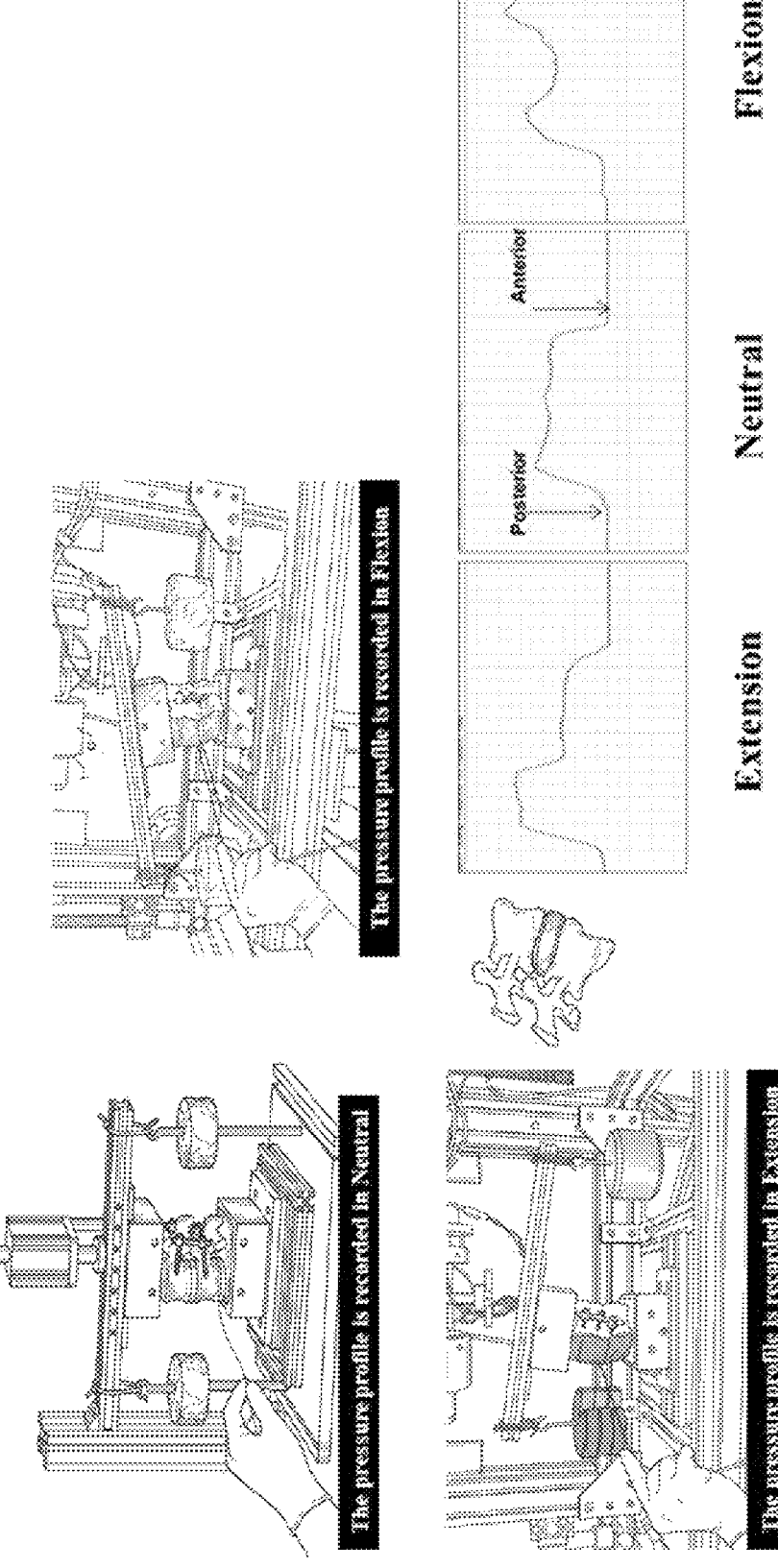
FIG. 14 is a graph showing a disc pressure profile in spinal fixation surgery using the bio-flexible spinal fixation apparatus according to the present invention.

As shown in the disc pressure profile graph illustrated in FIG. 14, a high pressure appears on the front side of the disc in the case of flexion motion, and a high pressure appears on the rear side of the disc in the case of extension motion. In the case of neutral, it is common that the pressure on the front and rear sides of the disc appears at a similar level. In the bio-flexible spinal fixation apparatus of the present invention, given that the operation of setting the fixation position of the rod 20 is correctly implemented, due to the characteristics in which the coil part 24 is wound around the center with a constant eccentricity d from the center of the straight part 22, a uniformly unloading effect that the pattern of the overall graph is similar appears even though the pressure value is slightly reduced compared to the normal disc pressure profile.

In addition, the spine does not move by only one specific segment, but the motion of each segment is combined overall to perform motions such as flexion and extension. Conventionally, the motion of each segment is called a range of motion (ROM), and it is a result of a general spinal biomechanical analysis that the ROM of the operated segment is relatively small, and the ROM of the upper and lower adjacent segments of the operated segment is larger. Therefore, the acceleration of adjacent segment degeneration above and below the operated segment is also due to these unnatural mechanical motions of the spine.

According to the structure of the rod 20 of the present invention in which the straight part 22 and the coil part 24 are configured to have a central eccentricity and a specific inclination, the ROM of the operated segment is relatively maximized, and the adjacent segment ROM is minimized, compared to surgery using a rigid rod. In addition, as a result of finite element analysis of a case in which the bio-flexible spinal fixation apparatus of the present invention is mounted on the posterior portion of the spine between the segments of the spine 500 and the interbody fusion cage is used in the anterior portion of the spine, it was demonstrated that the load sharing ratio between the anterior portion and the posterior portion approaches the normal load sharing mechanism ratio as a ratio of 7:3 or 7.5:2.5. As a result, it is possible to minimize the adjacent segment degeneration above and below the operated segment.

Explaining the operating method of the rod, since the coil part 24 is wound around the center with a certain eccentricity d from the center of the straight part 22 of the rod 20, the rod 20 is operated in such a way that the motion is greater in the case of the flexion which is the motion of bending the waist forward and the motion is smaller in the case of extension which is the motion of stretching the waist backward, thereby deriving results similar to the actual biomechanical movement of the spine.

Rather than the structure in which the center of the coil part is wound eccentrically with the center of the straight part, if the shape of the rod has the spring structure in which the coil part and the straight part are wound concentrically around the same central axis as in a general spring, since the degree or size of the motion appears similarly during the flexion and extension, the motion of the waist becomes unnatural.

However, by the coupling structure of the straight part and coil part of the rod according to the present invention, since the spine is prevented from being biased to one side and the bending of the waist when the spine is bent backward is further limited than the motion when the spine is bent forward, and the load sharing between a plurality of fused spinal segments is similar to the normal load sharing mechanism, thereby it realizes the effect of relieving the burden on the waist.

Hereinabove, specific embodiments of the present invention have been described. However, the spirit and scope of the present invention is not limited to these specific embodiments, and it will be understood by those of ordinary skill in the art that various modifications and variations are possible within the scope of not changing the gist of the present invention.

DESCRIPTION OF REFERENCE SIGNS

| | |
|---|---|
| 10: Screw pike | 12: Head part |
| 14: Receiving groove | 16a, 16b: Groove |
| 20: Rod | 22: Straight part |
| 24: Coil part | 26: Flat surface |
| 30: Set screw | 32: Wrench groove |
| 34: Through hole | 36: Wing part |
| 40: Washer | 42: Spherical projection |
| 44: Spherical groove | 500: Spine |

What is claimed is:

1. A bio-flexible spinal fixation apparatus, comprising:
a screw pike that includes a head part that has a receiving part penetrating in both sides and female threads formed on an inner circumferential surface of the receiving part and grooves formed in parallel at a bottom portion and a screw that extends to a bottom surface of the head part and is configured to be inserted into a spinal segment;

a rod that has a straight part seated in the groove of the screw pike and a coil part wound to be inclined by a specific angle based on a center separated by a predetermined distance with an eccentricity from a center of the straight part, wherein an upper surface of the straight part of the rod has a flat surface;

a set screw that has a fixing groove formed in the central portion and is fastened to the female thread of the head part of the screw pike to pressurize and fix the rod, wherein the set screw has the coupling hole smaller in size than a fixing groove at a lower end of the central portion; and a washer that has a spherical projection provided on an upper side of the central portion to fit into a coupling hole of the set screw and is formed in a plane on the bottom surface to be in close contact with the flat surface of the rod in order to uniformly share a vertical load applied by a tightening force of the set screw to the flat surface of the rod.

2. A bio-flexible spinal fixation apparatus, comprising:

a screw pike that includes a head part that has a receiving part penetrating in both sides and female threads formed on an inner circumferential surface of the receiving part and grooves formed in parallel at a bottom portion and a screw that extends to a bottom surface of the head part and is configured to be inserted into a spinal segment;

a rod that has a straight part seated in the groove of the screw pike and a coil part wound to be inclined by a specific angle based on a center separated by a predetermined distance with an eccentricity from a center of the straight part;

a set screw that has a fixing groove formed in the central portion and is fastened to the female thread of the head part of the screw pike to pressurize and fix the rod, wherein the set screw has the coupling hole smaller in size than a fixing groove at a lower end of the central portion; and a washer that has a spherical projection provided on an upper side of the central portion to fit into a coupling hole of the set screw and has a spherical groove having a size receiving a spherical surface of the rod formed on the bottom surface to uniformly share a vertical load applied by a tightening force of the set screw to the flat surface of the rod.

3. A bio-flexible spinal fixation system comprising:

first, second, and third pedicle screw arrays, each including:

pedicle screws configured to be arranged vertically on each side of a center line of a human body, and head parts having a plurality of opening grooves;

first and second rod arrays, each seated in one of the plurality of opening grooves of the head parts of the pedicle screws in the first, second and third pedicle screw arrays, wherein the rod arrays connect the pedicle screw arrays in a segmented form;

a fixing cap, fastened to the head parts of the pedicle screws in the first, second and third pedicle screw arrays, fixing the first and second rods of the rod arrays to prevent the first and second rods from being separated from the opening grooves;

wherein each of the first and second rods comprises:

a straight part, a coil part formed at a central portion of the straight part;

whereby the coil part is wound eccentrically in one direction while extending upward from the center of the straight part;

whereby the coil part is inclined in either the medial or lateral direction relative to an imaginary centerline of each pedicle screw when the surgical patient is in a prone position on an operating table.

4. The bio-flexible spinal fixation system of claim 3, wherein the opening grooves of the head parts of the first to third pedicle screws are formed of two, and when the coil parts of the first and second rods are symmetrically positioned in inner grooves of the two opening grooves based on the center line of the human body, the symmetrical coil parts are wound so as to be inclined laterally from the imaginary center line of the first to third pedicle screws.

5. The bio-flexible spinal fixation system of claim 3, wherein the opening grooves of the head parts of each of the first to third pedicle screws are formed of two, and when the coil parts of the first and second rods are symmetrically positioned in outer grooves of the two opening grooves based on the center line of the human body, the symmetrical coil parts are wound so as to be inclined medially from the imaginary center line of the first to third pedicle screws.

6. The bio-flexible spinal fixation system of claim 3, wherein an inclination of the coil parts of the first and second rods is 31.7°±5°.

7. The bio-flexible spinal fixation system of claim 3, wherein the opening grooves of the head parts of each of the first to third pedicle screws are formed in a shape corresponding to an appearance of the straight parts of the first and second rods.

8. The bio-flexible spinal fixation system of claim 7, wherein the straight parts of the first and second rods have a circular cross section but have a flat cross section with a flat upper surface, and the opening grooves of the head parts of each of the first to third pedicle screws is formed in a circular shape to receive a circular cross section of a shaft.

9. The bio-flexible spinal fixation system of claim 7, wherein the straight parts of the first and second rods are pressed so that lower surfaces of the straight parts have a circular cross section, and upper surfaces and left and right surfaces of the straight parts have a flat cross section, and the opening groove of the head part has a circular bottom portion and both side surfaces formed in the flat cross section to be formed to a size that receives a lower circular cross section and left and right flat cross sections of the straight part.

10. The bio-flexible spinal fixation system of claim 3, wherein a screw part is formed on inner circumferential surfaces of the opening grooves of the head parts of each of the first to third pedicle screws, and the fixing cap is formed with a set screw so as to be fastened to a threaded part of the opening groove.

11. The bio-flexible spinal fixation system of claim 10, further comprising:

a washer that has a spherical projection provided on an upper side of a central portion to fit into a coupling hole of the cylindrical portion and a spherical groove that is provided on a bottom surface thereof and has a size receiving a spherical surface of a rod to uniformly share a vertical load applied by a tightening force of the set screw to flat surfaces of the first and second rods, wherein the set screw is formed of a cylindrical portion
having a coupling hole penetrating through a central
portion.

* * * * *